(12) United States Patent
Takii et al.

(10) Patent No.: US 9,480,396 B2
(45) Date of Patent: Nov. 1, 2016

(54) OPHTHALMIC MEASUREMENT APPARATUS AND OPHTHALMIC MEASUREMENT PROGRAM

(71) Applicant: NIDEK CO., LTD., Gamagori, Aichi (JP)

(72) Inventors: Michihiro Takii, Aichi (JP); Noriji Kawai, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/554,466

(22) Filed: Nov. 26, 2014

(65) Prior Publication Data

US 2015/0150448 A1    Jun. 4, 2015

(30) Foreign Application Priority Data

Nov. 29, 2013   (JP) .................................. 2013-248476

(51) Int. Cl.
| | |
|---|---|
| *A61B 3/14* | (2006.01) |
| *A61B 3/10* | (2006.01) |
| *A61B 3/02* | (2006.01) |
| *A61B 3/107* | (2006.01) |
| *A61B 3/15* | (2006.01) |

(52) U.S. Cl.
CPC ............ *A61B 3/107* (2013.01); *A61B 3/1005* (2013.01); *A61B 3/14* (2013.01); *A61B 3/152* (2013.01)

(58) Field of Classification Search
USPC ................................................ 351/200–246
See application file for complete search history.

(56) References Cited

U.S. PATENT DOCUMENTS

| 5,592,246 A | * | 1/1997 | Kuhn | ...................... | A61B 3/107 |
| | | | | | 351/212 |
| 5,861,937 A | * | 1/1999 | Fujieda | ................... | A61B 3/152 |
| | | | | | 351/204 |

(Continued)

FOREIGN PATENT DOCUMENTS

| CN | 1989894 A | 7/2007 |
| CN | 103370002 A | 10/2013 |
| EP | 1057446 A2 | 12/2000 |
| EP | 1803390 A2 | 7/2007 |
| JP | 2003-111727 A | 4/2003 |

(Continued)

OTHER PUBLICATIONS

Communication issued on Apr. 8, 2015 by the European Patent Department in related Application No. 14195220.0.

(Continued)

*Primary Examiner* — Mohammed Hasan
(74) *Attorney, Agent, or Firm* — Sughrue Mion, PLLC

(57) ABSTRACT

There is provided an ophthalmic measurement apparatus 1 including: a keratoscopic projection optical system 10 that projects a pattern target toward a cornea Ec of a subject eye E; and an imaging optical system 20, the imaging device 27 of which captures second Purkinje images Rp1 and Rp2 that are target images formed due to the pattern target being reflected from a posterior corneal surface of the subject eye E. In the ophthalmic apparatus 1, a controller 100 executes a process (S9) of detecting the second Purkinje images Rp1 and Rp2 based on an imaging signal output from the imaging device 27, and an anterior chamber information acquisition process (S10) of acquiring information of the posterior corneal surface of the subject eye E based on the detected result of the detecting process.

20 Claims, 6 Drawing Sheets

(56) References Cited

U.S. PATENT DOCUMENTS

| | | |
|---|---|---|
| 6,193,371 B1 | 2/2001 | Snook |
| 6,382,796 B1 | 5/2002 | Ban |
| 2006/0028617 A1 | 2/2006 | Matsumura et al. |
| 2007/0146636 A1 | 6/2007 | Ishikura |
| 2009/0163898 A1* | 6/2009 | Gertner .................. A61B 3/113 606/4 |
| 2011/0075098 A1 | 3/2011 | Endo et al. |
| 2011/0090459 A1* | 4/2011 | Rathjen .................. A61B 3/107 351/212 |
| 2011/0242488 A1* | 10/2011 | Nakamura ............. A61B 3/152 351/208 |
| 2013/0003076 A1 | 1/2013 | Yoshida et al. |
| 2013/0286351 A1 | 10/2013 | Shimizu |

FOREIGN PATENT DOCUMENTS

| | | |
|---|---|---|
| JP | 2011-72604 A | 4/2011 |
| JP | 2012-55337 A | 3/2012 |
| JP | 2012-143492 A | 8/2012 |
| WO | 2009127442 A1 | 10/2009 |
| WO | 2011/122685 A1 | 10/2011 |

OTHER PUBLICATIONS

Communication dated May 27, 2016, from the State Intellectual Property Office of People's Republic of China in counterpart Application No. 201410717827.4.

* cited by examiner

OPHTHALMIC MEASUREMENT APPARATUS AND OPHTHALMIC MEASUREMENT PROGRAM

CROSS-REFERENCE TO RELATED APPLICATION

This application claims priority from Japanese Patent Application No. 2013-248476, filed on Nov. 29, 2013, the entire subject matter of which is incorporated herein by reference.

TECHNICAL FIELD

The present disclosure relates an ophthalmic measurement apparatus, which measures a subject eye, an ophthalmic measurement method and an ophthalmic measurement program.

BACKGROUND

A posterior corneal surface, for example, the curvature and shape of the posterior corneal surface may be measured as ophthalmic characteristics of a subject eye. For example, the curvature of the posterior corneal surface is used for calculating a corneal refractive power, and the calculated result is used for calculating an intraocular lens power. Conventionally, characteristics of the posterior corneal surface are acquired by analyzing a cross-sectional image of the cornea which is captured using apparatus such as a Scheimpflug camera and an anterior chamber OCT apparatus.

An example of such apparatus is disclosed in JP-A-2012-055337.

In the above-mentioned examples of the related art, a cross-sectional image of the cornea is required. Accordingly, a user is required to be prepared with an apparatus that captures a cross-sectional image of the cornea.

When the cornea is measured in a plurality of meridional directions using a Scheimpflug camera, an optical system should be turned so as to obtain a cross-sectional image at different angles, and thereby such apparatus results to have rather complicated configuration. Since an anterior chamber OCT requires an interference optical system and an optical scanner, the anterior chamber OCT apparatus is relatively expensive.

SUMMARY OF THE INVENTION

The present disclosure has been made in view of the above circumstances, and one of objects of the present disclosure is to provide an ophthalmic measurement apparatus and a method for measuring a cornea of a subject eye, which are capable of acquiring information of the posterior corneal surface of a subject eye using an apparatus with a simple configuration.

According to an illustrative embodiment of the present disclosure, there is provided an ophthalmic measurement apparatus including: a projection optical system configured to project a pattern target toward a cornea of a subject eye; an imaging optical system provided with an imaging device configured to capture an image of the subject eye, the image including a second Purkinje image, which is a target image formed due to the pattern target being reflected from a posterior corneal surface of the subject eye; a processor connected to the imaging device; and a memory storing computer readable instructions, when executed by the processor, causing the processor to function as: a detecting unit configured to detect the second Purkinje image from the image captured by the imaging device; and an acquiring unit configured to acquire posterior corneal surface information related to the posterior corneal surface of the subject eye based on the second Purkinje image detected by the detecting unit.

According to another illustrative embodiment of the present disclosure, there is provided a method for measuring cornea of a subject eye, the method including: projecting a pattern target toward a cornea of a subject eye; capturing an image of the subject eye, the image including a second Purkinje image, which is a target image formed due to the pattern target being reflected from a posterior corneal surface of the subject eye; detecting the second Purkinje image from the image of the subject eye; and acquiring posterior corneal surface information related to the posterior corneal surface of the subject eye based on the second Purkinje image detected from the image from the image of the subject eye.

According to the present disclosure, an ophthalmic measurement apparatus with a simple configuration can acquire information of a posterior corneal surface of a subject eye.

DETAILED DESCRIPTION

Hereinafter, an embodiment of the present disclosure will be described with reference to the accompanying drawings. First, a schematic configuration of an ophthalmic measurement apparatus 1 according to the embodiment will be described with reference to FIG. 1.

Figure 1:
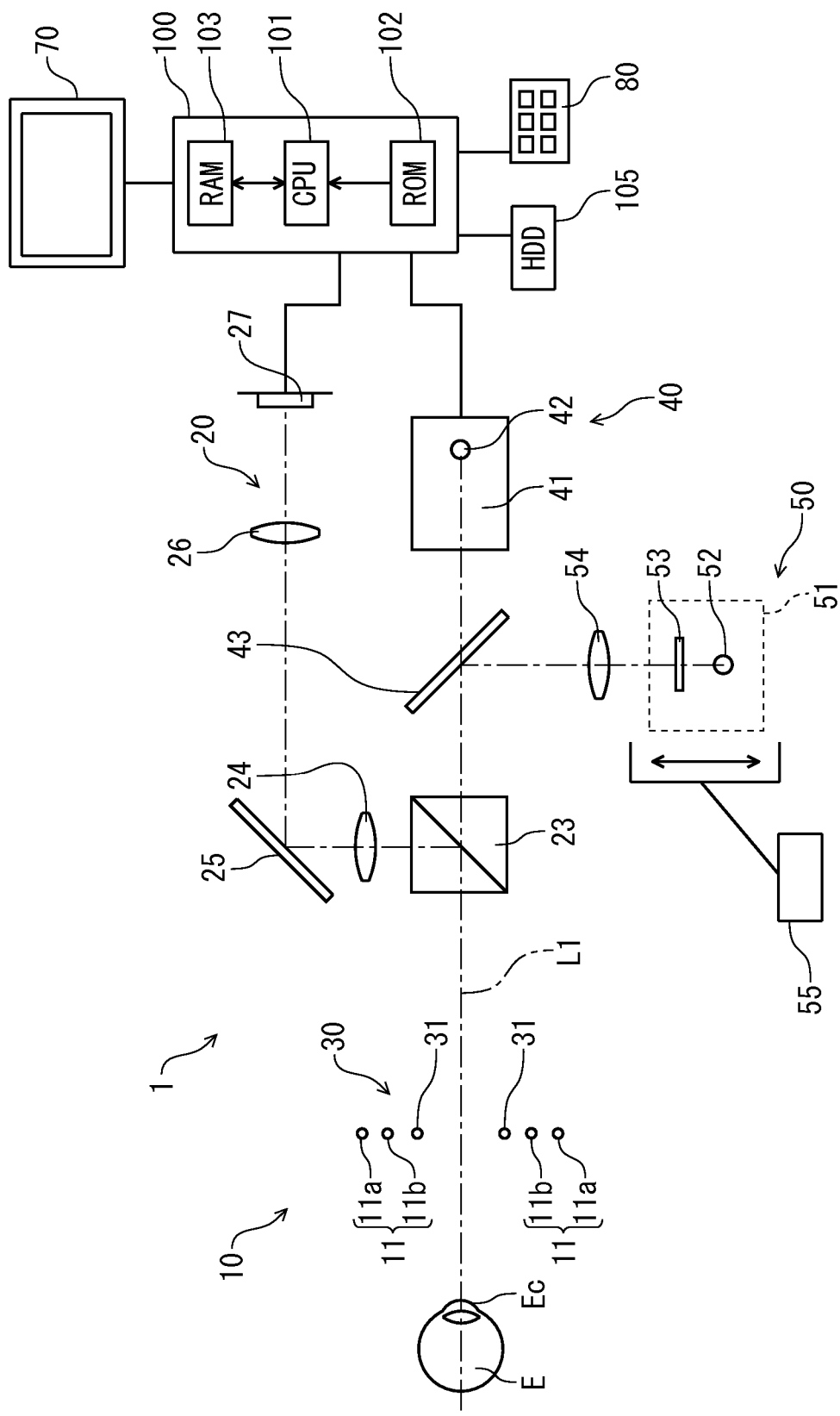
FIG. 1 is a schematic view illustrating a configuration of an ophthalmic measurement apparatus according to an embodiment.

The ophthalmic measurement apparatus 1 illustrated in FIG. 1 measures the posterior corneal surface of a subject eye E. As illustrated in FIG. 1, the ophthalmic measurement apparatus 1 is provided with a keratoscopic projection optical system 10; an imaging optical system (light receiving optical system) 20; and a controller 100. The ophthalmic measurement apparatus 1 of the embodiment has an alignment projection optical system 30; a second measurement optical system 40; and a fixation target projection optical system 50. These optical systems are built in a housing, which is not illustrated in the accompanying drawings A well-known alignment moving mechanism enables three-dimensional movement of the housing with respect to the subject eye. For example, the housing may be moved according to an instruction input from an examiner (user) through an operation console having user interface such as a joystick.

The keratoscopic projection optical system 10 projects (projects the light of) a pattern target (measurement target) on the cornea of the subject eye E. In the embodiment, the target from the keratoscopic projection optical system 10 is used to measure the posterior surface (back surface) of the cornea. For example, the shape, the curvature radius, and the refractive power of the posterior corneal surface and the like may be measured. For example, a corneal thickness, and an astigmatic axis angle for the posterior corneal surface may also be measured. As will be described later, the pattern target may be used to measure the anterior surface (front surface) of the cornea (for example, used to measure the shape, the curvature radius, the refractive power of the anterior corneal surface, a corneal thickness, and an astigmatic axis angle).

The keratoscopic projection optical system 10 has a light source 11. For example, the projection optical system 10 may project a ring-shaped target on the cornea of the eye E. In the embodiment, the light source 11 includes a first ring light source 11a and a second ring light source 11b. For example, a ring-shaped light source may be used as the first ring light source 11a and the second ring light source 11b, or each of the first ring light source 11a and the second ring light source 11b may adopt a configuration obtained by combining together a plurality of LEDs arranged so as to form a ring shape and a ring-shaped pattern opening disposed in front of the LEDs. Each of the ring light sources 11a and 11b is formed into a ring shape which has a measurement optical axis L1 as the center thereof. In the embodiment, two ring light sources 11a and 11b project two ring-shaped targets of different sizes, respectively.

Figure 2:
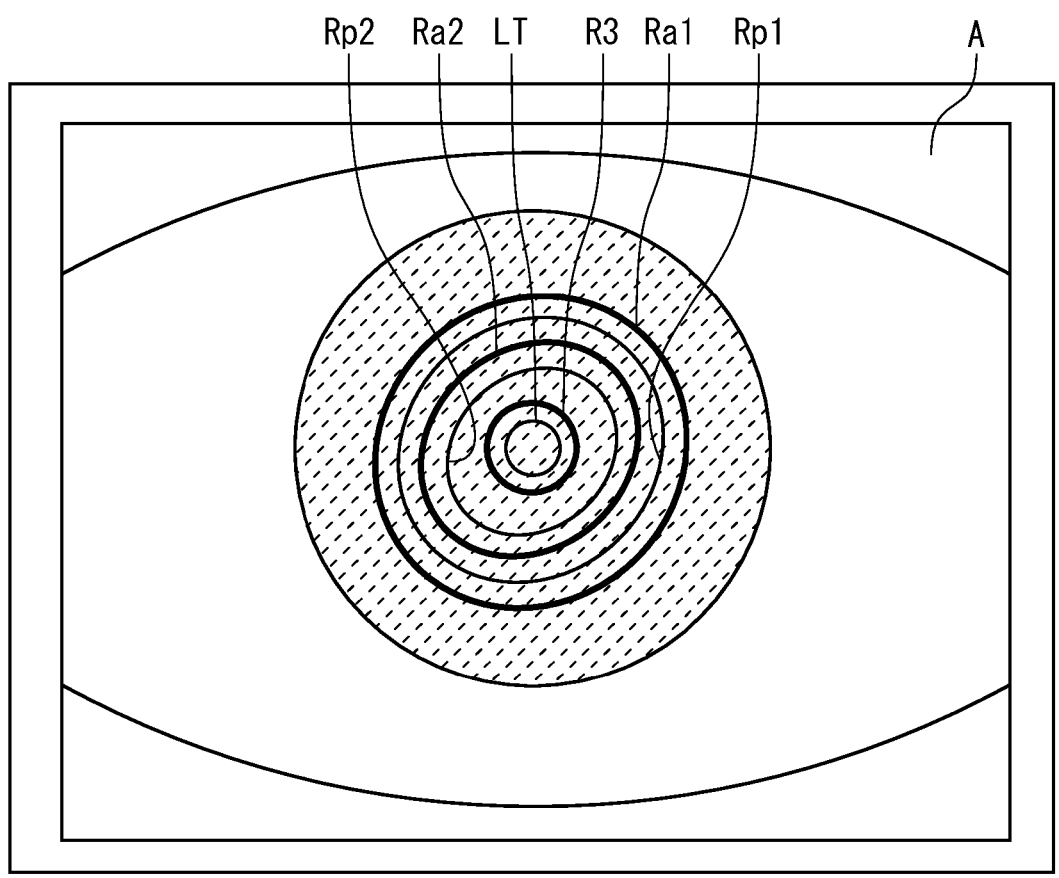
FIG. 2 is a schematic view of an anterior chamber image captured by the ophthalmic measurement apparatus.

As illustrated in FIG. 2, the anterior corneal surface reflects (and scatters) the light flux of the target projected from the first ring light source 11a, and a first ring-shaped Purkinje image Ra1 can be formed by the reflected light. The posterior corneal surface reflects (and scatters) the light of the target projected from the first ring light source 11a, and a second ring-shaped Purkinje image Rp1 can be formed by the reflected light. Typically, the luminance of the second Purkinje image is lower than that of the first Purkinje image. In the embodiment, the second Purkinje image Rp1 is formed inward of the first Purkinje image Ra1 due to the curve of a cornea Ec. Similarly, the anterior corneal surface reflects the light flux from the second ring light source 11b, and a first Purkinje image Ra2 can be formed by the reflected light. The posterior corneal surface reflects the light flux from the second ring light source 11b, and a second Purkinje image Rp2 can be formed by the reflected light.

In the embodiment, the first ring light source 11a has a diameter greater than that of the second ring light source 11b. The second Purkinje image Rp1 occurs on an outer circumference of the second Purkinje image Rp2. In the embodiment, the second Purkinje images Rp1 and Rp2 are mainly used to measure the cornea, which will be described later in detail.

In the embodiment, the position of the projection of the pattern target is displaced by alternately turning on the light sources. The two ring light sources 11a and 11b may be concurrently turned on. When the two ring light sources are concurrently turned on, the projection positions preferably do not overlap with each other. Only one of the two ring light sources 11a and 11b may be turned on. For example, the light source 11 may emit infrared light or visible light.

The shape and position of the light source 11 are not limited to the configuration in which the light source 11 is formed by the two ring light sources 11a and 11b. For example, the light source 11 may be a single ring light source. Moreover, the light source 11 may be three or more ring light sources. The light source 11 may be a plurality of point light sources. At this time, the light source 11 preferably includes at least three or more point light sources among the point light sources, which are disposed on the same circumference. The light source 11 may be an intermittent ring light source. That is, the examples of the pattern target include a pattern that is formed by three or more point targets which are concentrically disposed, a dot matrix target formed by point targets arranged in grid, an intermittent ring pattern, and the like, in addition to the ring-shaped target pattern of the embodiment.

The alignment projection optical system 30 projects an alignment target on the cornea of the subject eye E. The alignment projection optical system 30 has a light source 31. In the embodiment, the light source 31 is disposed inward of the light source 11 of the keratoscopic projection optical system 10. The light source 31 has a projection light source 31 (for example, λ=970 nm) that emits infrared light, and is used to project an alignment target on the cornea of the subject eye. An alignment target projected on the cornea is used for a position alignment (for example, automatic alignment, alignment detection, or a manual alignment) with respect to the subject eye. As illustrated in FIG. 2, in the embodiment, the alignment projection optical system 30 projects a ring target R3 as an alignment target. The ring target image R3 may be also used as a Mayer ring. The light source 31 of the alignment projection optical system 30 is also used as anterior chamber illumination optical system that project illumination light on the cornea of the subject eye E, which diagonally illuminates the anterior chamber. The projection optical system 30 may be further provided with an optical system so as to project parallel light on the cornea, and a forward and rearward alignment may be performed by the combination of the parallel light and finite light through the alignment projection optical system 30.

In the embodiment, the imaging optical system 20 includes a two-dimensional imaging device 27, and can capture an image of the front surface of the anterior chamber of the subject eye from a forward direction. More specifically, the imaging optical system 20 is provided with a dichroic mirror 23; an objective lens 24; a mirror 25; an imaging lens 26; and the two-dimensional imaging device 27. For example, the two-dimensional imaging device 27 may be disposed at a position conjugate with the anterior chamber of the subject eye. The imaging optical system 20 is disposed in such a manner that an optical axis of the imaging optical system 20 is coaxial with that of the fixation target projection optical system 50.

The dichroic mirror 23 (beam splitter) is an optical path splitting member that splits an optical path of the imaging optical system 20 from an optical path of the second measurement optical system 40 (the details will be described later).

Here, light from the keratoscopic projection optical system 10 and the alignment projection optical system 30 is reflected from the anterior chamber, and the reflected light is formed as an image (photodetected) on the imaging device (for example, two-dimensional imaging device) 27 via the optical path of the imaging optical system 20. Accordingly, the imaging optical system 20 captures an image of the anterior chamber that the keratoscopic projection optical system 10 irradiates with light, and thus the imaging optical system 20 can capture an anterior chamber image A that contains the target images (for example, the first Purkinje images Ra1 and Ra2, and the second Purkinje images Rp1 and Rp2) formed on the cornea Ec. The imaging optical system 20 captures an image of the anterior chamber that the alignment projection optical system 30 irradiates with light, and thus the imaging optical system 20 can capture the anterior chamber image A that contains the ring target image R3 formed on the cornea Ec.

The second measurement optical system 40 is arranged at a position on an optical path that transmits through the dichroic mirror 23 in the imaging optical system 20.

The second measurement optical system 40 is provided with a second measurement optical unit 41 and a dichroic mirror 43. The second measurement optical system 40 shares the dichroic mirror 23 with the imaging optical system 20. The second measurement unit 41 is configured to project second measurement light on the subject eye, and photodetects the reflected light. The second measurement unit 41 has a light source 42 that emits the second measurement light.

For example, the second measurement optical system 40 may be an eye axial-length measurement optical system (for example, the wavelength λ of the light source 42 is equal to 830 nm) that measures the axial length of the eye by detecting interference light resulting from measurement light and reference light, an eye refractive power measurement optical system (for example, the wavelength λ of the light source 42 is 870 nm) that measures an eye refractive power by detecting reflected light projected on the fundus of the subject eye, and the like.

The fixation target projection optical system 50 is arranged at a position on an optical path that is reflected by the dichroic mirror 43 in the second measurement optical system 40.

The fixation target projection optical system 50 is used to fix the vision of the subject eye E during a measurement. In the embodiment, the fixation target projection optical system 50 has a fixation target unit 51; a lens 54; and a fixation target position adjusting mechanism 55.

The fixation target unit 51 has a light source 52 and a target board 53. When light is emitted from the light source 52, a fixation target formed on the target board 53 is projected on the subject eye E via the lens 54 and the like. The fixation target position adjusting mechanism 55 enables to displace the fixation target unit 51 along an optical axis L4 of the fixation target projection optical system 50. Accordingly, the presentation position (presentation distance) of the fixation target with respect to the subject eye E is adjusted.

Subsequently, a control system will be described. In the ophthalmic measurement apparatus 1 of the embodiment, the controller 100 serves to perform overall control of the ophthalmic measurement apparatus 1 and to calculate a measurement result.

In the embodiment, the controller 100 is connected to the light source 11; the imaging device 27; the light source 31; the second measurement optical unit 41; the light source 52; the fixation target position adjusting mechanism 55; a monitor 70; a user interface 80; and a storage device 105.

The controller 100 is provided with a CPU 101; a ROM 102; and a RAM 103. The CPU 101 is a processing device (processor) for executing various processes of the ophthalmic measurement apparatus 1. The ROM 102 is a non-volatile storage device that stores a control program, fixed data, and the like. The RAM 103 is a rewritable volatile storage device. For example, the RAM 103 stores temporary data that the ophthalmic measurement apparatus 1 uses so as to capture an image of and measure the subject eye E.

The storage device 105 is a rewritable non-volatile storage device. In the embodiment, the storage device 105 stores at least a program for causing the controller 100 to execute an anterior chamber measurement process. The storage device 105 may store anterior chamber images captured by the ophthalmic measurement apparatus 1.

Here, a photodetection signal (imaging signal) output from the imaging device 27 is processed by the controller 100, and is displayed on the monitor 70. The controller 100 detects an alignment state of the subject eye E based on the photodetection signal output from the imaging device 27.

In this embodiment, the CPU 101 serves as a processor connected to the imaging device 27, and the ROM 102 and RAM 103 serves as a memory storing computer readable instructions, when executed by the processor, causing the processor to function as: a detecting unit configured to detect the second Purkinje images Rp1, Rp2 from the image captured by the imaging device 27; and an acquiring unit configured to acquire posterior corneal surface information related to the posterior corneal surface of the subject eye E based on the second Purkinje images Rp1, Rp2 detected by the detecting unit.

In the embodiment, the CPU 101 also functions a mode setting unit, an imaging control unit, a fixation target position control unit, and a projection control unit.

The mode setting unit may be configured to set an operational mode into one of: a first Purkinje image capturing mode in which the imaging optical system is set to capture the image of the subject eye for detecting the first Purkinje image; and a second Purkinje image capturing mode in which the imaging optical system is set to capture the image of the subject eye for detecting the second Purkinje image.

The imaging control unit may be configured to change imaging condition of the image captured by the imaging device in the imaging optical system in accordance with the operational mode being set by the mode setting unit.

The fixation target position control unit may be configured to control the fixation target position adjusting mechanism to set the position of the fixation target to be at a far point of the subject eye when the imaging device captures the image for detecting the second Purkinje image at least when the operational mode is set to the second Purkinje image capturing mode.

The projection control unit may be configured to control the projection optical system to selectively project at least one of the plurality of ring target patterns.

The operation of the ophthalmic measurement apparatus 1 having the above-mentioned configuration will be described.

Figure 3:
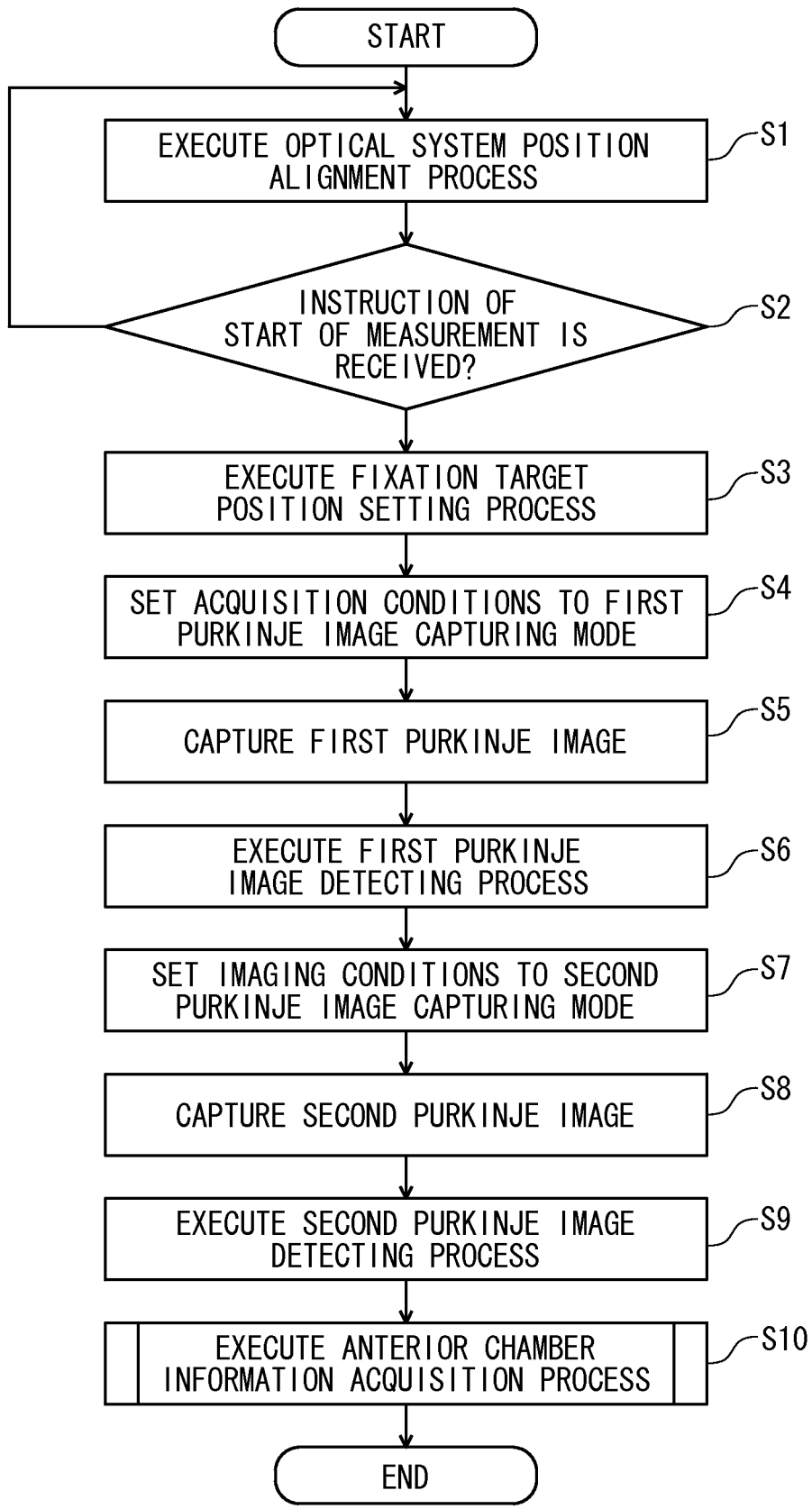
FIG. 3 is a flowchart illustrating a process of a CPU relative to the measurement operation of the ophthalmic measurement apparatus.

In the embodiment, an example of the operation of the apparatus relative to the measurement of the anterior chamber is illustrated with reference to a flowchart in FIG. 3. First, the CPU 101 performs an optical system position alignment process (S1). During the position alignment, the CPU 101 turns on the light source 31 of the alignment projection optical system 30, and displays a live image (observed image) of the subject eye E on the monitor 70 based on a photodetection signal that is output from the imaging device 27 in association with the turn-on of the light source 31. The CPU 101 electronically displays a reticle LT (refer to FIG. 2) on the monitor 70.

The CPU 101 detects the ring target R3 induced by the light source 31, based on an imaging signal from the imaging device 27. The CPU 101 controls to activate an actuator unit (not illustrated) which moves the optical systems of the ophthalmic measurement apparatus 1 in such a manner that the ring target R3 is disposed concentrically with the reticle LT, based on a detected result. The CPU 101 aligns the optical systems of the apparatus in a forward and rearward direction in such a manner that a distance between the apparatus and the corneal apex becomes a predetermined operational distance, based on an imaging signal from the imaging device 27.

The alignment may not necessarily be automatically performed. For example, the alignment may be performed based on an instruction input from the examiner. At this time, for example, the CPU 101 may receive the instruction input from the examiner through the user interface 80, which is provided with, for example, joystick, and may move the optical systems of the ophthalmic measurement apparatus 1 based on the instruction input.

The examiner can align the respective positions of the optical systems with each other before inputting an instruction of the start of a measurement via the user interface 80 (S2: No). The CPU 101 executes processes after step S3 based on the instruction of the start of a measurement from the examiner (S2: Yes).

In the embodiment, the presentation position (presentation distance) of the fixation target with respect to the subject eye E is set prior to measuring the anterior chamber (S3). At this time, the fixation target comes close to a far point of the subject eye E. For example, in the embodiment, the CPU 101 controls the fixation target position adjusting mechanism 55 based on position information of the far point of the subject eye, and disposes the fixation target at the far point of the subject eye E. As a result, the fixation prevents the subject eye from being adjusted. Accordingly, the anterior chamber is measured in a state where the pupil is less contracted. For example, the CPU 101 acquires the position information of the far point as follows. For example, if the second measurement unit 40 is configured to measure the position of the far point of the subject eye E (for example, to measure an eye refractive power), the ophthalmic measurement apparatus 1 may acquire the position information of the far point based on the measurement result of the second measurement unit 40. A measured result of the position of the far point of the subject eye E obtained by another inspection instrument may be transmitted to the ophthalmic measurement apparatus 1, or the examiner may directly input the position of the far point via the user interface 80, and thereby the ophthalmic measurement apparatus 1 may acquire the position information of the far point.

Subsequently, in the embodiment, the CPU 101 sets conditions (for example, states of the optical systems), under which the ophthalmic measurement apparatus 1 acquires a target pattern image, to a first Purkinje image capturing mode (first mode) (S4). In this mode, an apparatus main body (for example, the controller 100) acquires data used in a process of detecting the first Purkinje images Ra1 and Ra2 (for example, process of detecting the position and shape of the first Purkinje images). In the embodiment, for example, in the first Purkinje image capturing mode, an anterior chamber image containing the first Purkinje images Ra1 and Ra2 is captured (taken), which will be described later. In the process in step S4, the amount of light of the light flux output from the light source 11, a gain of the imaging device 27, and the like are preferably adjusted in such a manner that a clean anterior chamber image containing the first Purkinje images Ra1 and Ra2 is captured. In the process in step S4, light photodetected by the imaging device 27 may be limited by the replacement and disposition of a filter for adjusting the amount of light on the optical path of each of the keratoscopic projection optical system 10 and the imaging optical system 20.

Subsequently, the CPU 101 captures an anterior chamber image used in the process of detecting the first Purkinje images Ra1 and Ra2 (S5). In the process in step S5, the CPU 101 may selectively project at least one of a plurality of the ring target patterns. More specifically, the first Purkinje image Ra1 based on the light flux from the first ring light source 11a and the first Purkinje image Ra2 based on the light flux from the second ring light source 11b may be captured so as to be respectively contained in separate images by turning on the first ring light source 11a and the second ring light source 11b in turn, one at a time. The first Purkinje images Ra1 and Ra2 may be captured so as to be contained in a single image by concurrently turning on the two ring light sources 11a and 11b. When a plurality of the first Purkinje images are captured in a single image, the first Purkinje images preferably do not overlap with each other.

After the process in step S5, the CPU 101 executes a first Purkinje image detecting process (S6). In the embodiment, in the first Purkinje image detecting process (S6) and a second Purkinje image detecting process (S9), the first Purkinje images Ra1 and Ra2 are detected based on an imaging signal output from the imaging device 27. More specifically, the first Purkinje images Ra1 and Ra2 are detected using the image captured in the process in step S5. In the embodiment, target position information of each of the first Purkinje images Ra1 and Ra2 is acquired as a result (detected result) of the process in step S6. For example, the target position information may be two-dimensional position information of each of the first Purkinje images Ra1 and Ra2.

Various processes can be executed in step S6. For example, the first Purkinje images may be detected based on luminance information of the anterior chamber image. As illustrated in FIG. 2, each of the first Purkinje images Ra1 and Ra2 has a width in the meridional direction. For example, the position of each of the first Purkinje images Ra1 and Ra2 may be detected from a region which contains continuous luminance values greater than or equal to a predetermined threshold value in the meridional distribution of luminance of the image of the cornea. At this time, more specifically, the position of a peak value (maximum value) or the position of a median value of the distribution in the region, which contains the continuous luminance values greater than or equal to a predetermined threshold value, may be detected as the position of each of the first Purkinje images Ra1 and Ra2. For example, the CPU 101 makes the RAM 102, the storage device 105, and the like store the detected result. The detected result of the first Purkinje images Ra1 and Ra2 is not limited to the target position information, and for example, the detected result may be information of the anterior corneal surface. For example, the information of the anterior corneal surface may be the curvature radius, the three-dimensional shape, or the power of the anterior corneal surface.

Subsequently, in the embodiment, the CPU 101 sets conditions (or acquisition conditions, and for example, states of the optical systems), under which the ophthalmic measurement apparatus 1 captures a target pattern image, to a second Purkinje image capturing mode (second mode) (S7). In this mode, the ophthalmic measurement apparatus 1 acquires data used in a process of detecting the second Purkinje images Rp1 and Rp2 (for example, process of detecting the position and shape of the second Purkinje images). In the embodiment, for example, in the second Purkinje image capturing mode, an anterior chamber image containing the second Purkinje images Rp1 and Rp2 is captured (taken). In the process in step S7, the amount of light of the light flux output from the light source 11, a gain of the imaging device 27, and the like are preferably adjusted in such a manner that a clean image containing the second Purkinje images Rp1 and Rp2 is captured. For example, the CPU 101 may increase the value of at least one of the amount of light from the light source 11 and the gain of the imaging device 27 in the first Purkinje image capturing mode.

In the process in step S7, the optical systems (for example, the alignment projection optical system 30 and the second measurement optical system 40) other than the keratoscopic projection optical system 10 are preferably prevented from irradiating light on the subject eye E, which will be described later in detail. For example, the CPU 101 may reduce the amount of light for projecting a fixation target output from the light source 52 so as to reduce the contraction of the pupil resulting from glare. At this time, the anterior chamber illumination (for example, the light source 31) may be turned off. That is, the second Purkinje images are preferably captured, and it may not be possible to confirm each portion of the anterior chamber on the image.

For example, the reflection of light from the fundus preferably prevents transillumination (light applied to the cornea from the fundus side). For example, the amount of light from each of the light source 31, the light source 42, and the like may be reduced. As a result, it is easy to capture the second Purkinje images Rp1 and Rp2 due to differences between background and the images.

Subsequently, the CPU 101 captures an anterior chamber image used in the process of detecting the second Purkinje images Rp1 and Rp2 (S8). In the process in step S8, the CPU 101 may selectively project at least one of a plurality of the ring target patterns. More specifically, the second Purkinje image Rp1 based on the light flux from the first ring light source 11a and the second Purkinje image Rp2 based on the light flux from the second ring light source 11b may be captured so as to be respectively contained in separate images by turning on the two ring light sources 11a and 11b in turn. At this time, one of the second Purkinje images Rp1 and Rp2 can be prevented from overlapping with a reflected image formed by the light flux from other light sources. Accordingly, in a subsequent second Purkinje image detecting process (S9), good detection of the second Purkinje images Rp1 and Rp2 is easy.

The second Purkinje images Rp1 and Rp2 may be captured so as to be contained in a single image by concurrently turning on the two ring light sources 11a and 11b. The image contains not only the second Purkinje images but also other reflected images (the first Purkinje images Ra1 and Ra2, and the like) of the target light flux. For this reason, when a plurality of the second Purkinje images are captured in a single image, the second Purkinje images preferably do not overlap with the other reflected images.

After the process in step S8, the CPU 101 executes the second Purkinje image detecting process (S9). In the embodiment, in the second Purkinje image detecting process (S9), the second Purkinje images are detected based on an imaging signal output from the imaging device 27. More specifically, the second Purkinje images are detected using the image captured in the process in step S8. In the embodiment, position and shape information (for example, coordinate data for the location of each of the images) of each of the second Purkinje images Rp1 and Rp2 is acquired as a result (detected result) of the process in step S9. For example, more specifically, a detected result is acquired by storing the detected result in the RAM 102.

Various processes can be executed in step S9. For example, also in the process in step S9 similar to the process in step S6, the second Purkinje images may be detected based on the luminance information of the anterior chamber image. Each of the second Purkinje images Rp1 and Rp2 has a width in the meridional direction. For example, the position of each of the second Purkinje images Rp1 and Rp2 may be detected from a region which contains continuous luminance values greater than or equal to a predetermined threshold value in the meridional distribution of luminance of the image of the cornea. The image acquired in the process in step S8 contains at least the first Purkinje images. Typically, the first Purkinje image is bright and distinct compared to the second Purkinje image. For example, the second Purkinje images Rp1 and Rp2 may be detected from a region containing a low peak luminance, with respect to a region that contains the first Purkinje image Ra1 and Ra2 in the meridional distribution of luminance. Typically, since the second Purkinje images are formed inward of (close to the optical axis) the first Purkinje images, the second Purkinje images Rp1 and Rp2 may be detected from a region that contains a peak occurring close to the optical axis L1, with respect to the region that contains the first Purkinje images Ra1 and Ra2 in the meridional distribution of luminance. Since each of the second Purkinje images Rp1 and Rp2 has a width in the meridional direction, the detailed position of each of the second Purkinje images Rp1 and Rp2 may be detected based on a distribution shape. For example, the position of a peak value (maximum value) or the position of a median value of the distribution may be detected as the position of each of the second Purkinje images Rp1 and Rp2.

Subsequently, the CPU 101 executes an anterior chamber information acquisition process (S10). In the anterior chamber information acquisition process (S10) of the embodiment, at least information of the posterior corneal surface is acquired as anterior chamber information based on the detected result of the second Purkinje images Rp1 and Rp2.

Figure 4:
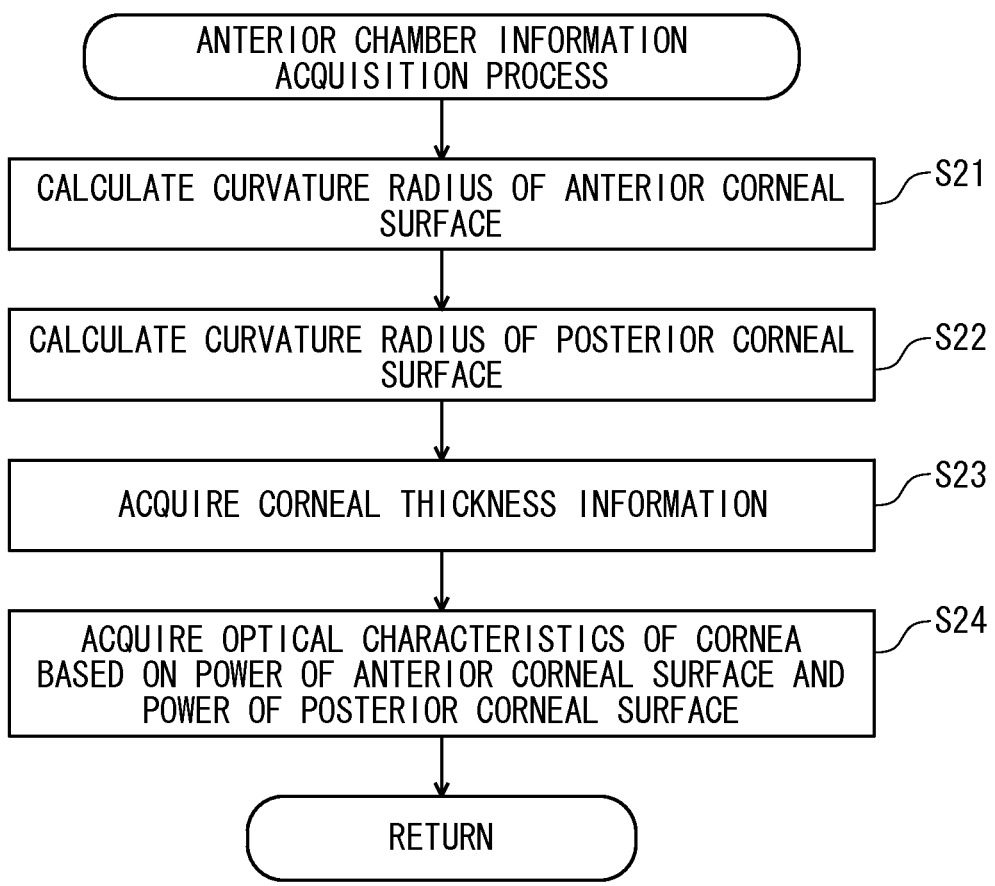
FIG. 4 is a flowchart illustrating an anterior chamber information acquisition process.

Here, an example of the anterior chamber information acquisition process will be described with reference to FIG. 4. In the anterior chamber information acquisition process (S10) of the embodiment, first, the CPU 101 calculates a curvature radius r1 of an anterior corneal surface Ec1 (S21). For example, it is possible to obtain the curvature radius r1 of the anterior corneal surface Ec1 based on the first Purkinje images Ra1 and Ra2 detected in the process in step S6. Specifically, there is a technique of obtaining the corneal curvature radius r1 based on the image height (for example, distance between the position (for example, the center of an image) of the optical axis L1 on the image and the first Purkinje images Ra1 and Ra2 under the assumption that the optical axis L1 passes through the center of the cornea) of each of the first Purkinje images Ra1 and Ra2. For example, with regard to details of this technique, refer to JP-A-2003-111727 filed by the present applicant.

In the embodiment, since each of the first Purkinje images Ra1 and Ra2 has a ring shape, it is possible to obtain the curvature radius r1 of a cornea Ec in an arbitrary meridional direction thereof. For this reason, as illustrated in the embodiment, it is possible to obtain the curvature radiuses r1 in a plurality of meridional directions.

In the embodiment, since the plurality of first Purkinje images Ra1 and Ra2 having different diameters are detected, it is possible to obtain a curvature radius from the detected result of the first Purkinje images Ra1 and Ra2.

Subsequently, the CPU 101 calculates a curvature radius r2 of a posterior corneal surface Ec2. For example, it is possible to obtain the curvature radius r2 of the posterior corneal surface Ec2 from the detected result of the second Purkinje images Rp1 and Rp2 obtained in the process in step S9, and from the curvature radius r1 of the anterior corneal surface Ec1 obtained in the process in step S21.

Figure 5:
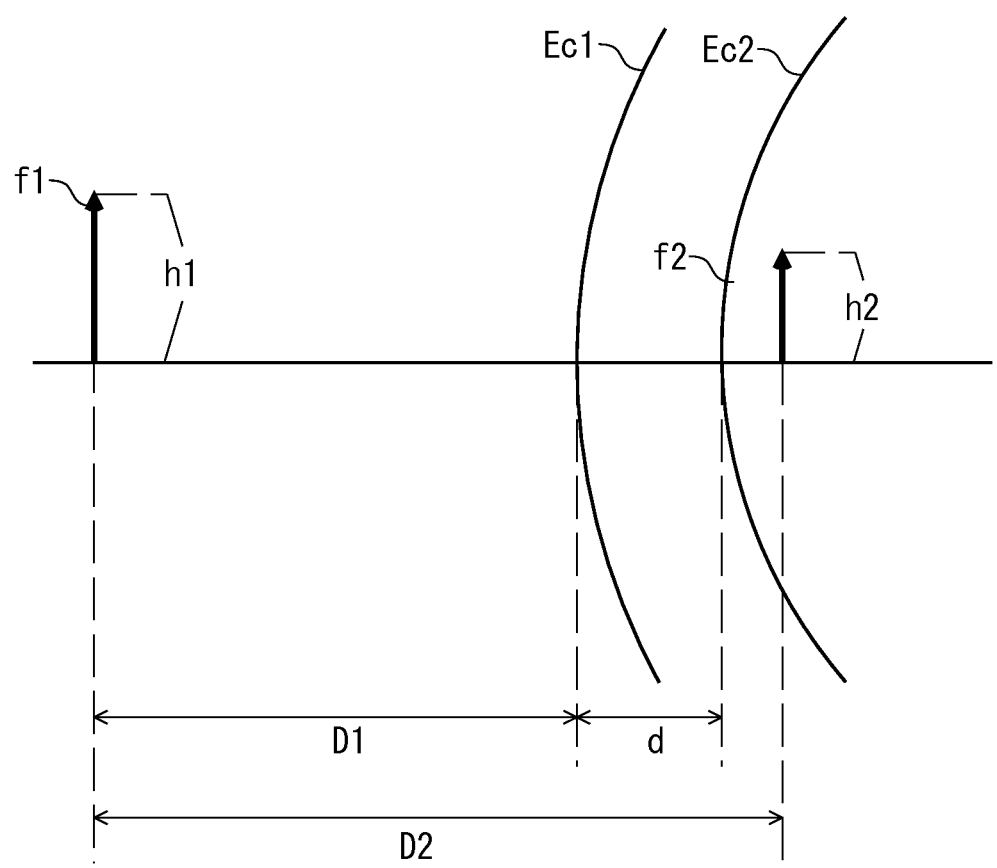
FIG. 5 is a schematic view describing a method of calculating a curvature radius of a posterior corneal surface.

Here, an example of a method of obtaining the curvature radius r2 of the posterior corneal surface Ec2 will be described with reference to FIG. 5. Here, the paraxial approximation is illustrated for descriptive purposes. In FIG. 5, a posterior-surface reflected image f2 of an object f1 is formed on the posterior corneal surface Ec2 under the assumption that the optical axis L1 passes through the center of the cornea. In FIG. 5, the tip of an arrow indicative of the object f1 indicates the position of the light source 11 (the first ring light source 11a or the second ring light source 11b). Accordingly, an object height h1 indicates a distance from the optical axis L1 to the light source 11. In contrast, the tip of an arrow indicative of the posterior-surface reflected image f2 indicates the position of a ring image that is formed by the light source 11 positioned at the tip of the arrow indicative of the object height h1. That is, an image height h2 of the posterior-surface reflected image f2 indicates a distance from the optical axis L1 to the ring image formed on the posterior corneal surface Ec2.

In FIG. 5, D1 indicates a distance from the object f1 to the anterior corneal surface Ec1. D2 indicates a distance from the object f1 to the posterior-surface reflected image f2. d is a corneal thickness (an example of corneal thickness information) at the reference position of the cornea. Here, d is the corneal thickness of a center corneal portion, and indicates a corneal thickness at a position through which the optical axis L1 passes. In the embodiment, the distance D1 is set to a fixed value obtained as a result of the optical system position alignment process (S1). For example, the corneal thickness d may be a value obtained by well-known pachymetry such as an ultrasound measurement method. A corneal pachymetry optical system may be provided in the secondary measurement optical system 40, and a measured result thereof may be used as the corneal thickness d.

Here, for example, it is possible to express the image height h2 using Expression (1) shown below. Hereinafter, the image height h2 indicates an image height when the object height h1 is equal to 1.

$$h2 = \beta \times \left[\left(1 - \frac{d}{n} \times \frac{n-1}{r1}\right) - D2 \times \left\{-\left(\frac{n-1}{r1}\right) + \left(\frac{d}{n} \times \frac{n-1}{r1}\right) \times \left(\frac{-2n}{r2}\right)\right\}\right] \quad (1)$$

The value n indicates a corneal refractive index. The value β is a correction coefficient for a magnification (or magnitude) of an image. More specifically, β corrects the influence of refraction by the cornea. For example, it is possible to express D2 and β using Expressions (2) and (3) below.

$$D2 = \frac{-D1 - \frac{d}{n}\left(1 - D1 \times \frac{n-1}{r1}\right)}{-\left[1 - D1 \times \frac{n-1}{r1} + \left\{-D1 - \frac{d}{n}\left(1 - D1 \times \frac{n-1}{r1}\right)\right\} \times \frac{-2n}{r2}\right]} \quad (2)$$

$$\beta = \frac{n}{nD2 + d} \times \left(\frac{\frac{nD2 + d}{n}}{-1 + \frac{nD2 + d}{n} \times \frac{1-n}{r1}}\right) \quad (3)$$

For example, a measured value based on the result obtained in the second Purkinje image detecting process (S9) is used as the image height h2. For this reason, it is possible to obtain the value of the curvature radius r2 of the posterior corneal surface Ec2 from Expression (1).

Here, the paraxial approximation is illustrated, but corrections or modifications can also be made to the above-mentioned expressions depending on an actual design of the apparatus.

In the process in step S22, the curvature radius r2 of the posterior corneal surface may be obtained by methods other than the calculation made by the CPU 101. For example, the CPU 101 may obtain the curvature radius r2 of the posterior corneal surface Ec2, using a table in which corneal parameters (for example, corneal thickness information and anterior surface curvature information) and the curvature radius r1 of the posterior corneal surface Ec2 are associated with each other. In one of the methods, a table is pre-stored in a storage device such as the storage device 105, and the table stores the curvature radius r2 of the posterior corneal surface Ec2 in association with the value of each of the curvature radiuses r1 of the anterior corneal surface Ec1 and a reference corneal thickness d. For example, the curvature radius r2 in the table may be a value obtained by the above-mentioned expressions. At this time, the CPU 101 refers to the table, and acquires a value from the table as the curvature radius r2 of the posterior corneal surface Ec2, in which the value from the table corresponds to the curvature radius r1 of the anterior corneal surface Ec1 obtained in the process in step S21 and the reference corneal thickness d.

The curvature and the curvature radius of the posterior corneal surface may be obtained each for different meridional directions, or may be obtained by averaging multiple curvature and curvature radius obtained each for different meridional directions.

Sequential description will be made with reference to the flowchart illustrated in FIG. 4. Subsequently, the CPU 101 acquires corneal thickness information (S23). For example, information indicative of a thickness distribution of the cornea in a specific meridional direction may be acquired as the corneal thickness information. For example, it is possible to obtain a thickness distribution of the cornea in a single meridional direction from values for the curvature radius r1 of the anterior corneal surface Ec1, the curvature radius r2 of the posterior corneal surface Ec2, and the reference corneal thickness d in the single meridional direction. In the process in step S23, information indicative of a thickness distribution of the entirety of the cornea may be acquired based on a thickness distribution of the entirety of the cornea in the plurality of meridional directions.

Subsequently, in the embodiment, the CPU 101 obtains a corneal refractive power based on the respective curves of the anterior corneal surface and the posterior corneal surface (S24). For example, the corneal refractive power is expressed as the power (P(θ)) of the cornea Ec, or in a form of {spherical power (S), cylindrical surface power (C), astigmatic axis angle (A)}. In the embodiment, a value is acquired by combining information (for example, power and/or the value of each of S, C, and A) of the power of the anterior corneal surface Ec1 and information (for example, power and/or the value of each of S, C, and A) of the power of the posterior corneal surface Ec2. In the embodiment, a combined value is obtained which is obtained by a power vector method. Typically, it is possible to express the power P(θ) using Expression (4) below.

$$P(\theta) = S + C[\sin^2(\theta - A)] \quad (4)$$

For example, it is possible to obtain the value of each of S, C, and A from the values of corneal curvatures in the steepest meridional direction and the flattest meridional direction when a ring image formed on the cornea is subject to elliptic approximation, and from axial angles on the steepest meridian and the flattest meridian. Accordingly, it is possible to obtain a power P2 of the posterior corneal surface Ec2 and the like based on the detected result of the second Purkinje images Rp1 and Rp2 formed on the posterior corneal surface Ec2. In addition, it is possible to obtain a power P1 of the anterior corneal surface Ec1 and the like based on the detected result of the first Purkinje images Ra1 and Ra2 formed on the anterior corneal surface Ec1.

The power P(θ) can be converted as follows.

$$P(\theta) = J_{45}\sin 2\theta + J_{180}\cos 2\theta + M \quad (5)$$

$$\text{wherein} \begin{cases} J_{45} = -\dfrac{C}{2}\sin 2A \\ J_{180} = -\dfrac{C}{2}\cos 2A \\ M = S + \dfrac{C}{2} \end{cases}$$

Here, the values of $J_{45}$, $J_{180}$, and M calculated for the power P1 are indicated by $J1_{45}$, $J1_{180}$, and M1, respectively, and the values of $J_{45}$, $J_{180}$, and M calculated for the power P2 are indicated by $J2_{45}$, $J2_{180}$, and M2, respectively. It is possible to express the values of $J_{45}$, $J_{180}$, and M for a combined power value Pmix(θ) by the following expression (6).

$$\begin{cases} J_{45} = J1_{45} + J2_{45} \\ J_{180} = J1_{180} + J2_{180} \\ M = M1 + M2 \end{cases} \quad (6)$$

A combined value of the values of the power (refractive power value), the spherical power (S), the cylindrical surface power (C), and the astigmatic axis angle (A) is obtained by putting a result from Expression (6) into Expression (5). The calculation of a combined value is not limited to the above-mentioned method. For example, a combined value of a ray trace power and the like may be obtained.

In the embodiment, the execution of the process in step S24 ends the cornea information acquisition process. As a result, the process of the flowchart illustrated in FIG. 3 ends.

As described above, in the embodiment, the CPU 101 acquires the information of the posterior corneal surface Ec2 (the curvature radius r2 of the posterior corneal surface Ec2, the corneal thickness distribution information, the power of the cornea Ec, and the like) based on the result of the process (S9) of detecting the second Purkinje images formed on the posterior corneal surface Ec2. Accordingly, the ophthalmic measurement apparatus 1 of the embodiment can acquire the information of the posterior corneal surface Ec2 without necessarily requiring an apparatus such as an anterior chamber OCT apparatus or a Scheimpflug camera which captures a cross-sectional image of the anterior chamber.

When the information of the posterior corneal surface is acquired from the cross-sectional image captured by an anterior chamber OCT apparatus, a Scheimpflug camera, or the like, an edge (boundary) of a cross section of the cornea in the image is detected. For example, the position of an edge of the posterior corneal surface in the image is specified as the position of the posterior corneal surface. However, typically, it is difficult to exactly specify the position of an edge of an object through image processing. The reason for this is that the position of detection of an edge of the same object changes depending on imaging conditions such as the amount of illumination light, even when an image of the same object is captured. In particular, it is considered that errors between an actual posterior corneal surface and the position of detection of an edge in a cross-sectional image of a subject eye occur depending on the optical characteristics (light transmittance of the cornea and the like) of the anterior chamber.

In contrast, the embodiment illustrates an example in which the posterior corneal surface is detected based on a distribution shape of a luminance distribution in each of the meridional directions in the image that contains the second Purkinje images. The distribution shape is dependent on the amount of illumination light, the optical characteristics of the anterior chamber, and the like, and the distribution shape is unlikely to be affected by the conditions such as the position of a peak value (maximum value) of the distribution and a median value of the curve containing a peak value. Accordingly, in the embodiment, the ophthalmic measurement apparatus 1 can acquire more exact information of the posterior corneal surface Ec2 when acquiring the information of the posterior corneal surface from a cross-sectional image.

When the curvature of the posterior corneal surface is obtained, the curvature of the posterior corneal surface is preferably calculated using the corneal thickness of the subject eye E. Since a corneal pachymetry optical system is provided as the second measurement optical system, the use of another apparatus is not necessarily required. For example, the corneal pachymetry optical system has a configuration disclosed in JP-A-2012-143492.

Also in this case, the corneal pachymetry optical system preferably can measure a corneal thickness at one or more points of the cornea, and the provision of a complicated optical system such as a Scheimpflug camera with a rotating mechanism or an anterior chamber OCT necessitating a two-dimensional scanner is not necessarily required.

In the embodiment, a combined power of the cornea is obtained as the information of the posterior corneal surface Ec2. When a compounded power is obtained from a cross-sectional image, the ophthalmic measurement apparatus 1 obtains an exact compounded power. Accordingly, for example, the power obtained by the ophthalmic measurement apparatus 1 contributes to the selection of an appropriate power of an intraocular lens (IOL) for a subject eye.

It is difficult to cleanly form the second Purkinje images Rp1 and Rp2. In contrast, in the embodiment, in the second Purkinje image capturing mode in which the second Purkinje images are detected and an image of the anterior chamber is acquired, the CPU 101 increases the amount of light from the light source 11 that projects the target light flux, or the gain of the photodetection element 27, compared to at least the first Purkinje image capturing mode. As a result, it is easy to obtain image data containing clean second Purkinje images Rp1 and Rp2 in the second Purkinje image capturing mode. Accordingly, in the second Purkinje image detecting process (S9), good detection of the second Purkinje images Rp1 and Rp2 is easy.

The iris of the subject eye E is a region, in which the luminance changes complicatedly. For this reason, when the second Purkinje images Rp1 and Rp2 are formed so as to overlap with the iris, there is a problem in that it is difficult to detect the second Purkinje images Rp1 and Rp2. In contrast, in the embodiment, in the second Purkinje image capturing mode, the CPU 101 reduces the amount of visible light which is applied to the subject eye E from the fixation target projection optical system 50, compared to at least the first Purkinje image capturing mode. Accordingly, in the second Purkinje image capturing mode, the contraction of the pupil resulting from glare is reduced. As a result, the second Purkinje images Rp1 and Rp2 are prevented from being formed at positions in which the second Purkinje images Rp1 and Rp2 overlap with the iris. Accordingly, with the ophthalmic measurement apparatus 1 of the embodiment, good detection of the second Purkinje images Rp1 and Rp2 is easy.

In the embodiment, vision fixation is performed so as to capture an anterior chamber image containing the second Purkinje images Rp1 and Rp2, using the fixation target disposed at the far point of the subject eye E. Accordingly, it is possible to capture the anterior chamber image in a state where the pupil is less contracted. As a result, the second Purkinje images Rp1 and Rp2 are prevented from being formed at the positions in which the second Purkinje images Rp1 and Rp2 overlap with the iris, and with the ophthalmic measurement apparatus 1, good detection of the second Purkinje images Rp1 and Rp2 is easy.

In the above description, the ophthalmic measurement apparatus 1 according to the embodiment is described, however, a configuration of the ophthalmic measurement apparatus 1 is not limited to those described in the above, and various modifications can be made thereto.

For example, typically, in addition to the first and second Purkinje images described in the embodiment, third and fourth Purkinje images are known as Purkinje images that are formed due to the light flux projected on the subject eye E being reflected from the anterior chamber. The third and fourth Purkinje images are respectively formed by the light flux reflected from the anterior lens surface and the posterior lens surface. Here, since the posterior lens surface reflects light less than the anterior lens surface does, when the second Purkinje images are detected from the anterior chamber image, the fourth Purkinje images are unlikely to become problematic. In contrast, the anterior lens surface reflects light more than the posterior lens surface does. As a result, third Purkinje images having the same level of brightness as that of the second Purkinje images may occur.

In contrast, for example, the keratoscopic projection optical system 10 (an example of a light projection optical system) may be configured so as to project a target pattern which is asymmetrical with respect to the meridian (center of an optical axis) of the cornea. In addition, the second Purkinje image capturing process (for example, the process in step S9) may be configured in such a manner that the second Purkinje images are detected from the upright reflected image of the target light flux. In an example of the configuration in which a target pattern is projected asymmetrically with respect to the meridian of the cornea, the ring light sources 11a and 11b may be partially (or intermittently) turned on. The ring light sources 11a and 11b may be replaced with a plurality of point light sources or the like which are disposed asymmetrically with respect to the meridian of the cornea.

Figure 6:
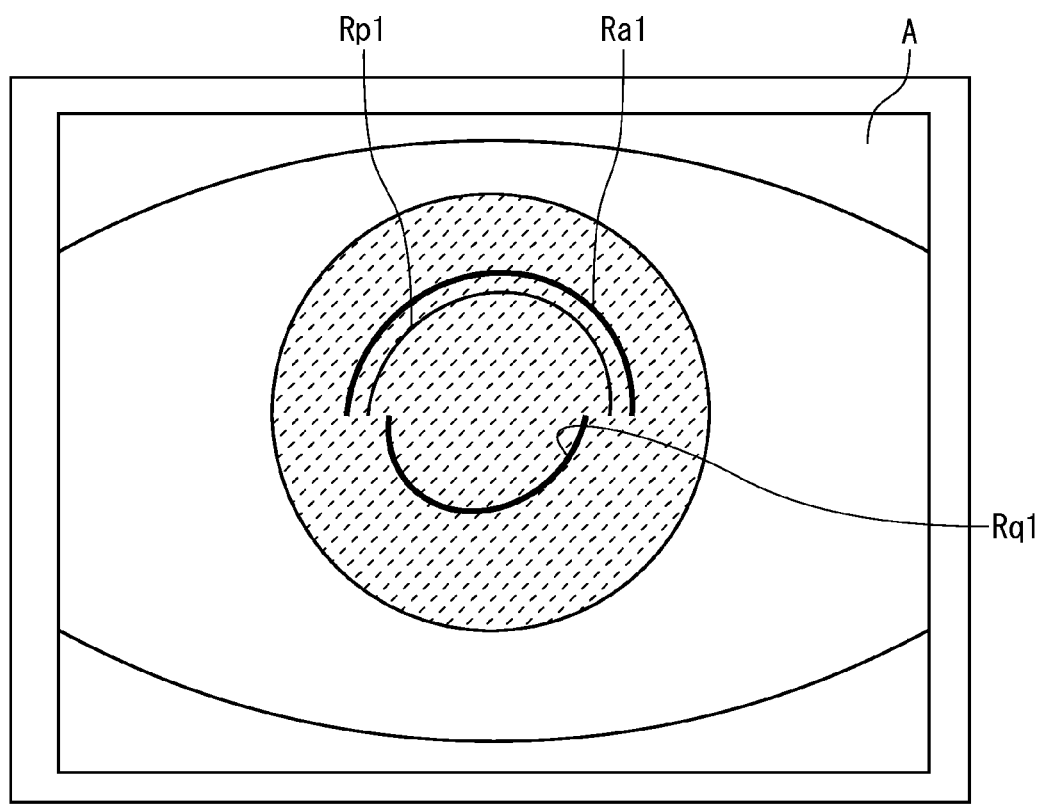
FIG. 6 is a schematic view of an anterior chamber image according to a modification example.

FIG. 6 illustrates an anterior chamber image captured in a state where only a higher half portion of the light source 11 (here, the first ring light source 11a) is turned on, as an example. In the example illustrated in FIG. 6, since the second Purkinje image is an upright reflected image, a second Purkinje image Rp is formed on the higher half portion of the cornea Ec. In contrast, a third Purkinje image Rq1 is an inverted reflected image. For this reason, in the example illustrated in FIG. 6, the third Purkinje image Rq1 is formed on a lower half portion of the cornea Ec. At this time, for example, a range of detection of the second Purkinje image Rp in the image may be limited to a range (in this example, corneal portion or higher half portion of the image) of the formation of the upright reflected image so as to detect the second Purkinje image Rp from the upright reflected image. As a result, it is possible to reduce a probability of the CPU 101 erroneously detecting the third Purkinje image as the second Purkinje image.

Not only the keratoscopic projection optical system 10 but also the alignment projection optical system 30 may be used as projection optical system for target light flux that forms a Purkinje image. In the embodiment, when the alignment projection optical system 30 is also used as a projection optical system for the target light flux, an anterior chamber image may be captured by turning on light sources in turn, one at a time. An anterior chamber image may be captured by alternately turning on the light source 11a and the light source 31, and the light source 11b in such a manner that two adjacent light sources (for example, the light source 11a and the light source 11b, and the light source 11b and the light source 31) are not concurrently turned on. Accordingly, the Purkinje images (the first Purkinje image and the second Purkinje image) formed by the light sources are prevented from overlapping with Purkinje images formed by other light sources. As a result, the apparatus detects each of the Purkinje images well.

In the embodiment, the corneal thickness of the center corneal portion is used as a corneal thickness at the reference position of the cornea; however, the corneal thickness is not limited to the corneal thickness at the reference position of the cornea, and a corneal thickness in a region away from the center of the cornea may be used as the corneal thickness at the reference position.

In the embodiment, when the first Purkinje images Ra1 and Ra2 and the second Purkinje images Rp1 and Rp2 are captured, the anterior chamber illumination (for example, the light source 31) may be turned off. That is, an image is preferably captured from which it is possible to detect position and shape information of each of the Purkinje images, and it is not necessary to capture an image from which it is possible to confirm each portion of the anterior chamber, for example, the position and shape of the pupil.

In the embodiment, the fixation target projection optical system 50 is described as an example of an auxiliary projection optical system that is controlled by the CPU 10 and projects illumination light on the subject eye E. However, the ophthalmic measurement apparatus 1 may be configured to be provided with, as the auxiliary projection optical system, one or more of other types of optical system that projects illumination light, which is different from the pattern target, on the subject eye E, in a case where the light has an influence on detection of the second Purkinje images Rp1 and Rp2. The auxiliary projection optical system may include: the alignment projection optical system 30 configured to project an alignment target on the cornea of the subject eye E; an anterior chamber illumination optical system configured to project illumination light on the cornea of the subject eye E; and a measurement optical system configured to project measurement light on the subject eye for measuring optical characteristics of the subject eye E. In the embodiment, the alignment projection optical system 30 is configured to serve as the anterior chamber illumination optical system, and the second measurement optical system 40 serves as the measurement optical system.

In the embodiment, the second Purkinje images Rp1 and Rp2 are detected from single piece of image obtained by capturing an anterior chamber image. However, the detection of the second Purkinje images Rp1 and Rp2 is not necessarily limited to that in the embodiment. For example, in the second Purkinje image capturing mode, a plurality of images, each of which having the same position of a pattern target, may be captured, and the CPU 101 may generate a sum image from these images. Thereafter, a process (for example, the process in step S9) of detecting the second Purkinje images Rp1 and Rp2 from the sum image may be performed. Since the sum image containing the clean second Purkinje images is obtained by summing the plurality of images, good detection of the second Purkinje images Rp1 and Rp2 is easy. The first Purkinje images Ra1 and Ra2 may be detected from a sum image. In a second Purkinje image capturing mode setting process (S7), the number of images summed is preferably set in such a manner that the number of images (the number of captured images) summed for detecting the second Purkinje images Rp1 and Rp2 is greater than that for detecting the first Purkinje images Ra1 an Ra2.

In the embodiment, the respective imaging conditions of the first Purkinje image capturing mode and the second Purkinje image capturing mode are different from each other; however, the first Purkinje images and the second Purkinje images may be captured under the same conditions. For example, the first Purkinje images and the second Purkinje images may be detected from the same image.

In the embodiment, in the processes in steps S6 and S9, the CPU 101 performs an image analysis process as an example of the Purkinje image detecting process; however, the present invention is not necessarily limited to that in the embodiment. For example, in at least one of the processes in steps S6 and S9, the Purkinje images may be detected based on position information of the Purkinje images on the image which is input via the user interface 80 by the examiner who confirms the anterior chamber image displayed on the monitor 70 or the like.

In the embodiment, the information of the posterior corneal surface is acquired by the ophthalmic measurement apparatus 1, but the present invention is not necessarily limited to that in the embodiment. For example, it is possible to obtain the information of the posterior corneal surface by transmitting the captured result (for example, image data) of the second Purkinje images to a general-purpose computer, and causing the computer to execute an analysis process. For example, when the information of the posterior corneal surface is acquired from the image data of the second Purkinje images and the image data of the first Purkinje images, an analysis program causing a processor of a computer to execute the processes in steps S6, S9, and S10 illustrated in FIG. 3 may be provided in a hard disk of the computer or the like which stores a program for obtaining the information of the posterior corneal surface. Also in this case, the information of the posterior corneal surface is obtained similarly to the ophthalmic measurement apparatus 1 of the embodiment.

What is claimed is:

1. An ophthalmic measurement apparatus comprising:
a projection optical system configured to project a pattern target toward a cornea of a subject eye;
an imaging optical system provided with an imaging device configured to capture an image of the subject eye, the image including a second Purkinje image, which is a target image formed due to the pattern target being reflected from a posterior corneal surface of the subject eye;
a processor connected to the imaging device; and
a memory storing computer readable instructions, when executed by the processor, causing the processor to function as:
a detecting unit configured to detect the second Purkinje image from the image captured by the imaging device;
an acquiring unit configured to acquire posterior corneal surface information related to the posterior corneal surface of the subject eye based on the second Purkinje image detected by the detecting unit;
wherein the projection optical system is configured to selectively project one of a plurality of pattern targets on cornea to have an asymmetric shape with respect to a center of the cornea;
the processor controls the projection optical system to selectively project one of the pattern targets before performing detection of the second Purkinje image; and
the processor detects the second Purkinje image from an upright reflected image of the selectively projected asymmetric pattern target.

2. The ophthalmic measurement apparatus according to claim 1,
wherein the imaging device captures the image of the subject eye further including a first Purkinje image, which is a target image formed due to the pattern target being reflected from an anterior corneal surface of the subject eye,
wherein the detecting unit is configured to detect the first Purkinje image from the image captured by the imaging device, and
wherein the acquiring unit is configured to acquire anterior corneal surface information related to the anterior corneal surface of the subject eye based on the first Purkinje image detected by the detecting unit.

3. The ophthalmic measurement apparatus according to claim 2,
wherein the acquiring unit is configured to acquire the posterior corneal surface information based on the first Purkinje image and the second Purkinje image detected by the detecting unit.

4. The ophthalmic measurement apparatus according to claim 2,
wherein the acquiring unit is configured to acquire the posterior corneal surface information based on the second Purkinje image detected by the detecting unit, the anterior corneal surface information acquired by the acquiring unit, and corneal thickness information related to corneal thickness of the subject eye at a reference position.

5. The ophthalmic measurement apparatus according to claim 4 further comprising:
a corneal pachymetry optical system configured to measure the corneal thickness of the subject eye at the reference position.

6. The ophthalmic measurement apparatus according to claim 5,
wherein the acquiring unit is configured to acquire a corneal thickness distribution of the subject eye as the posterior corneal surface information based on:
curvature information of the posterior corneal surface of the subject eye obtained from the second Purkinje image;
curvature information of the anterior corneal surface of the subject eye obtained from the first Purkinje image; and
the corneal thickness of the subject eye at the reference position.

7. The ophthalmic measurement apparatus according to claim 2, wherein the acquiring unit is configured to acquire a power of the cornea by applying vector synthesis on a power of the anterior corneal surface and a power of the posterior corneal surface.

8. The ophthalmic measurement apparatus according to claim 1,
wherein the acquiring unit is configured to acquire a curvature radius of the posterior corneal surface as the posterior corneal surface information.

9. The ophthalmic measurement apparatus according to claim 1,
wherein the memory further stores computer readable instructions, when executed by the processor, causing the processor to function as:
a mode setting unit configured to set an operational mode into one of: a first Purkinje image capturing mode in which the imaging optical system is set to capture the image of the subject eye for detecting the first Purkinje image; and a second Purkinje image capturing mode in which the imaging optical system is set to capture the image of the subject eye for detecting the second Purkinje image; and
an imaging control unit configured to change imaging condition of the image captured by the imaging device in the imaging optical system in accordance with the operational mode being set by the mode setting unit.

10. The ophthalmic measurement apparatus according to claim 9,
wherein the imaging control unit is configured to set at least one of an amount of projection light of the pattern target projected by the projection optical system and a gain of the imaging device in the second Purkinje image capturing mode to be larger than in the first Purkinje image capturing mode.

11. The ophthalmic measurement apparatus according to claim 9 further comprising:
an auxiliary projection optical system configured to project light that is different from the pattern target toward a cornea of a subject eye,
wherein the imaging control unit is configured to control the auxiliary projection optical system to reduce amount of the light when the second Purkinje image capturing mode is set by the mode setting unit than in the first Purkinje image capturing mode.

12. The ophthalmic measurement apparatus according to claim 11,
wherein the auxiliary projection optical system comprises at least one of:
a fixation target projection optical system configured to project a fixation target on the subject eye;
an alignment projection optical system configured to project an alignment target on the cornea of the subject eye;
an anterior chamber illumination optical system configured to project illumination light on the cornea of the subject eye; and
a measurement optical system configured to project measurement light on the subject eye for measuring optical characteristics of the subject eye.

13. The ophthalmic measurement apparatus according to claim 11,
wherein the light projected from the auxiliary projection optical system contains light which is to be reflected from the fundus and applied to the cornea.

14. The ophthalmic measurement apparatus according to claim 11,
wherein the auxiliary projection optical system is configured to project a fixation target on the subject eye, the fixation target being emitted from a visible light source.

15. The ophthalmic measurement apparatus according to claim 9 further comprising:
a fixation target position adjusting mechanism configured to adjust a position of a fixation target projected to the subject eye,
wherein the memory further stores computer readable instructions, when executed by the processor, causing the processor to function as:
a fixation target position control unit configured to control the fixation target position adjusting mechanism to set the position of the fixation target to be at a far point of the subject eye when the imaging device captures the image for detecting the second Purkinje image at least when the operational mode is set to the second Purkinje image capturing mode.

16. The ophthalmic measurement apparatus according to claim 1,
wherein the projection optical system is configured to project a plurality of concentric ring target patterns as the pattern targets,
wherein the detecting unit is configured to detect the second Purkinje image for each of the ring target patterns, and
wherein the acquisition unit is configured to acquire posterior corneal surface information for posterior corneal surface regions different in a meridional direction of the cornea.

17. The ophthalmic measurement apparatus according to claim 16,
wherein the memory further stores computer readable instructions, when executed by the processor, causing the processor to function as:
a projection control unit configured to control the projection optical system to selectively project at least one of the plurality of ring target patterns.

18. A method for measuring cornea of a subject eye, the method comprising:
projecting a pattern target toward a cornea of a subject eye;
capturing an image of the subject eye, the image including a second Purkinje image, which is a target image formed due to the pattern target being reflected from a posterior corneal surface of the subject eye;
detecting the second Purkinje image from the image of the subject eye; and
acquiring posterior corneal surface information related to the posterior corneal surface of the subject eye based on the second Purkinje image detected from the image from the image of the subject eye;
wherein the projecting step includes selectively projecting one of a plurality of pattern targets on cornea to have asymmetric shape with respect to a center of the cornea before detecting the second Purkinje image; and
the detecting step includes detecting the second Purkinje image from an upright reflected image of the selectively projected asymmetric pattern target.

19. The ophthalmic measurement apparatus according to claim 1, wherein the second Purkinje image is detected from a summed image created by summing up a plurality of images captured for a same position of the pattern target.

20. The ophthalmic measurement apparatus according to claim 1, wherein the projection optical system is provided with a plurality of light sources including a ring light source and a point light source that includes a plurality of point light source elements arranged to have a ring shape, the plurality of light sources being controlled to be selectively turned on to create the plurality of pattern targets.

* * * * *